United States Patent [19]

Quemada et al.

[11] Patent Number: 5,623,066
[45] Date of Patent: Apr. 22, 1997

[54] CUCUMBER MOSAIC VIRUS COAT PROTEIN GENE

[75] Inventors: Hector D. Quemada; Jerry L. Slightom, both of Kalamazoo, Mich.

[73] Assignee: Asgrow Seed Company, Kalamazoo, Mich.

[21] Appl. No.: 365,973

[22] Filed: Dec. 28, 1994

Related U.S. Application Data

[63] Continuation of Ser. No. 168,974, Dec. 16, 1993, abandoned, which is a continuation-in-part of Ser. No. 805,489, Dec. 9, 1991, abandoned, which is a continuation-in-part of Ser. No. 499,474, filed as PCT/US88/04321, Dec. 8, 1988, abandoned, which is a continuation of Ser. No. 135,591, Dec. 21, 1987, abandoned.

[51] Int. Cl.$^6$ .......................... C12N 15/40; C12N 15/82; A01H 5/00
[52] U.S. Cl. .................... 536/23.72; 435/172.3; 435/252.3; 435/320.1; 435/418; 435/411; 435/415; 435/419; 800/205
[58] Field of Search .............. 435/172.3, 240.4, 435/320.1, 252.3; 536/23.72; 800/205

[56] References Cited

U.S. PATENT DOCUMENTS 4,394,443  7/1983  Weissman et al. .................... 435/6

FOREIGN PATENT DOCUMENTS 223452  5/1987  European Pat. Off. ..
279433  8/1988  European Pat. Off. ..

OTHER PUBLICATIONS

An, G. et al, (1985) "New Cloning Vehicles for Transformation of Higher Plants", Embo. J. 4:277–284.
Dodds, J.A. et al (1985) "Cross Protection Between Strains of Cucumber Mosaic Virus: Effect of Host and Type of Inoculum on Accumulation of Virions and Double–Stranded RNA of the Challenge Strain", Virology 144:301–309.
Pietrzak, M. et al, (1986) "Expression in Plants of Two Bacterial Antibiotic Resistant Genes After Protoplast Transformation with a New Plant Expression Vector", Nuc. Acids Res. 14:5857–5868.
Quemada, H. et al, "The nucleotide sequence of cDNA clones from RNA 3 of cucumber mosaic virus strains C and WL" J. Cell. Biochem. Suppl 12c, 1988, p. 287, (see abstract Y 333).
Gonsalves, DR et al, "Tomato (Lycopersicon esculentum) white leaf: The relation of an apparent satellite RNA and cucumber mosaic virus" Biological Abstracts, vol. 75, 1983, abstract 83219 & Phytopathology 72 (12): 1533–1538.
Rothstein, SJ et al, "Promoter cassettes, antibiotic–resistance genes, and vectors for plant transformation", Gene vol. 53, Nos. 2,3, 1987 Amsterdam, pp. 153–161, (see p. 157).
Trulson, AJ et al, "Transformation of cucumber (Cucumis sativus L.) plants with Agrobacterium rhizogenes" Chemical Abstracts, vol. 106, 1987 abstract 11458ob (see p. 165) & Theor. Appl. Genet. 1986, 73(1) 11–15.
Edwards, M, et al, "Grouping of seven biologically defined isolates of cucumber mosaic virus by peptide mapping" Chemical Abstracts, vol. 99, 1983 (see p. 431) abstract 191204w & Phytopathology 1983 73(8) 1117–20.
Lakshman, DK et al, "Comparative analysis of cell–free translational products of some strains of cucumber mosaic virus" Biological Abstracts, see abstract 6536 & Phytopathology 74 (7); 1984, 848.
Gould et al. 1982 Eur. J. Biochem. 126:217–226.
Dodds et al. 1985 Virology 144:301–309.
Abel et al. 1986 (May) Science 232:738–743.

*Primary Examiner*—Patricia R. Moody
*Attorney, Agent, or Firm*—Fitzpatrick, Cella, Harper & Scinto

[57] ABSTRACT

A DNA fragment which encodes the coat protein of cucumber mosaic virus strain c (CMV-C), the method of preparing it, its use to prepare transgenic plants and transgenic plants containing it are provided.

7 Claims, 1 Drawing Sheet

FIGURE 1

```
   1 GAATTCCCGC CGCAATCGGG AGTTCTTCCG CGTCCCGCTC CGAAGCCTTC
  51 AGACCGCAGG TGGTTAACGG TCTTTAGTCA CTTTGGTGCG TATTAGTATA
 101 TAAGTATTTG TGAGTCTGTA CATAATACTA TATCTATAGA GTCCTGTGTG
 151 AGTTGATACA GTAGACATCT GTGACGCGAT GCCGTGTTGA GAAGGGATCA
 201 CATCTGGTTT TAGTAAGCCT ACATCATAGT TTTGAGGTTC AATTCCTCTT
 251 ACTCCCTGTT GAGTACCTTA CTTTCTCATG GATGCTTCTC CGACGAGATT
 301 GTCGTTATTG TCTACTGACT ATATAGAGAG TGTGTGTGCT GTGTTTCTC
 351 TTTTGTGTCG TAGAATTGAG TCGAGTCATG GACAAATCTG AATCAACCAG
 401 TGCTGGTCGT AACCATCGAC GTCGTCCGCG TCGTGGTTCC CGCTCCGCCC
 451 CCTCCTCCGC GGATGCTAAC TTTAGAGTCT TGTCGCAGCA GCTTTCGCGA
 501 CTTAATAAGA CGTTAGCAGC TGGTCGTCCA ACTATTAACC ACCCAACCTT
 551 TGTAGGGAGT GAACGCTGTA GACCTAGGTA CACGTTCACA TCTATTACCC
 601 TAAAGCCACC AAAAATAGAC CGTGAGTCTT ATTACGGTAA AAGGTTGTTA
 651 CTACCTGATT CAGTCACGGA ATATGATAAG AAGCTTGTTT CGCGCATTCA
 701 AATTCGAGTT AATCCTTTGC CGAAATTTGA TTCTACCGTG TGGGTGACAG
 751 TCCGTAAAGT TCCTGCCTCC TCGGACTTAT CCGTTGCCGC CATCTCTGCT
 801 ATGTTCGCGG ACGGAGCCTC ACCGGTACTG GTTTATCAGT ATGCCGCATC
 851 TGGAGTCCAA GCCAACAACA AACTGTTGTT TGATCTTTCG GCGATGCGCG
 901 CTGATATAGG TGACATGAGA AAGTACGCCG TCCTCGTGTA TTCAAAAGAC
 951 GATGCGCTCG AGACGGACGA GCTAGTACTT CATGTTGACA TCGAGCACCA
1001 ACGCATTCCC ACATCTGGAG TGCTCCCAGT CTGATTCCGT GTTCCCAGAA
1051 CCCTCCCTCC GATCTCTGTG GCGGGAGCTG AGTTGGCAGT TCTACTACAA
1101 ACTGTCTGGA GTCACTAAAC GTTTTACGGT GAACGGGTTG TCCATCCAGC
1151 TTACGGCTAA AATGGTCAGT CGTGGAGAAA TCCACGCCAG CAGATTTACA
1201 AATCTCTGAG GCGCCTTTGA AACCATCTCC TAGGTTTCTT CGGAAGGGCT
1251 TCGGTCCGTG TACCTCTAGC GCAACGTGCT AGTTTCAGGG TACGGGTGCC
1301 CCCCCACTTT CGTGGGGGCC TCCAAAAGGA GACCAAAAAA AAAAAAAAA
1351 AAAAAAAAAA AAAAAAAAAA AAAAAAAAAA AAAAAAAAAA AAAAAAAAAA
1401 AAAAAAAAAA AAAAAAAAAA GAATTC
```

5,623,066

CUCUMBER MOSAIC VIRUS COAT PROTEIN GENE

CROSS REFERENCE TO RELATED APPLICATION

This application is a file wrapper continuation of U.S. Ser. No. 08/168,974, filed Dec. 16, 1993, now abandoned; which is a continuation-in-part of U.S. Ser. No. 07/805,489, filed Dec. 9, 1991, abandoned; which is a continuation-in-part of U.S. Ser. No. 07/499,474, filed Jun. 14, 1990, abandoned; which is a continuation of international application PCT/US88/04321, filed Dec. 8, 1988; which is a continuation of U.S. Ser. No. 07/135,591, filed Dec. 21, 1987, abandoned.

FIELD OF INVENTION

This invention relates to a coat protein gene of cucumber mosaic virus strain c (CMV-C). More specifically the invention relates to a process for preparing a DNA-fragment encoding said gene as well as its incorporation into a transformation vector and to its use to produce transformed plant cells and transformed plants which are resistant to CMV viral infections.

BACKGROUND OF THE INVENTION

Cucumber mosaic virus (CMV) is a single-stranded (+) RNA plant virus which has a functionally divided genome. The virus genome contains four RNA species designated RNAs 1–4; and for CMV strain Q 3389 nucleotides (nt), 3035 nt, 2193 nt and 1027 nt, respectively (Peden and Symons, Virology, 53, 487–492, 1973; Gould and Symons, 1982 Eur. J. Biochem., 126, 217–226; Rezaian et al., 1984 Eur. J. Biochem. 143, 227–284; Rezaian et al., 1985 Eur. J. Biochem. 150, 331–339). Only RNAs 1–3 are required for infectivity (Peden and Symons, 1973) because the coat protein, which is encoded by RNA 4, is also encoded by RNA 3. Translations of CMV RNAs yield a 95KDal polypeptide from RNA 1, a 94kDal polypeptide from RNA 2, (Gordon et al., 1983 Virology 123, pp 284–295) and two polypeptides from RNA 3: its 5' end encodes a 35KDal polypeptide, and its 3' end encodes a 24.5kDal polypeptide (Gould and Symons, 1982). The 24.5kDal polypeptide is identical to that encoded by RNA 4 and is the coat protein.

The CMV coat protein gene does not contain the signals necessary for its expression once transferred and integrated into a plant genome. It must be engineered to contain a constitutive promoter 5' to its translation initiation codon (ATG) and a poly(A) addition signal (AATAAA) 3' to its translation termination codon. Several promoters which function in plants are available, but we believe that the best promoters are the constitutive promoters from CaMV, the Ti genes nopaline synthase (Bevan et al., 1983 Nucleic Acids Res. II 369–385) and octopine synthase (Depicker et al., 1982 J. Mol. Appl. Genet. 1, 561–564), and the bean storage protein gene phaseolin. The poly (A) addition signals from these genes are suitable for our purposes as well.

INFORMATION DISCLOSURE

Plants that are resistant to virus diseases and methods for producing them are described in EP 223,452.

An, G., et al. (1985) "New Cloning Vehicles for Transformation Of Higher Plants". EMBO J. 4:277–284; Dodds, J. A., et al. (1985) Cross protection between strains of cucumber mosaic virus: effect of host and type of inoculum on accumulation of virions and double-stranded RNA of the challenge strain. Virology 144:301–309. Pietrzak, M., et al. (1986) "Expression in plants of two bacterial antibiotic resistant genes after protoplast transformation with a new plant expression vector" Nuc. Acids Res 14:5857–5868.

SUMMARY OF THE INVENTION

This invention provides: A DNA fragment which encodes the coat protein from the C strain of cucumber mosaic virus (CMV-C).

A plant transformation vector comprising a DNA fragment which encodes the coat protein from CMV-C, a CaMV 35S promoter of cauliflower mosaic virus and the polyadenylation signal of either the cauliflower mosaic virus 35S gene or the Phaseolin seed storage protein gene.

A bacterial cell containing a plant transformation vector comprising a DNA fragment which encodes the coat protein from CMV-C, a CaMV 35S promoter of cauliflower mosaic virus and the polyadenylation signal of either the cauliflower mosaic virus 35S gene or the Phaseolin seed storage protein gene.

A transformed plant cell containing a DNA fragment which encodes the coat protein from CMV-C, a CaMV 35S promoter of cauliflower mosaic virus and the polyadenylation signal of either the cauliflower mosaic virus gene or the phaseolin seed storage protein gene.

A plant comprising transformed cells containing a DNA fragment which encodes the coat protein from CMV-C, a CaMV 35S promoter of cauliflower mosaic virus and the polyadenylation signal of either the cauliflower mosaic virus gene or the Phaseolin seed storage protein gene. Transformed plants of this invention include beets, citrus fruit, corn, cucumber, peppers, potatoes, soybean, squash and tomatoes. Especially preferred are members of the Cucurbitaceae (squash, cucumber, i.e.,) and Solanaceae (peppers, tomatoes, i.e.) family.

A process for producing virus-resistant plants comprising propagating a plant expressing the coat protein gene from the C strain of cucumber mosaic virus. Especially preferred is the process for producing members of the Cucurbitaceae and Solanaceae families.

BRIEF DESCRIPTION OF THE FIGURES

FIG. 1 shows the sequence of a cDNA encoding the coat protein of cucumber mosaic virus strain C.

DESCRIPTION OF THE PREFERRED EMBODIMENT

FIG. 1 and Charts 1 to 5 are set forth to illustrate the construction of this invention.

FIG. 1 shows the sequence of a pUC19 clone containing a DNA fragment which encodes the CMV-coat protein. Certain conventions are used to illustrate plasmids and DNA fragments as follows:

(1) The single line charts represent both circular and linear double-stranded DNA.

(2) Asterisks (*) indicate that the molecule represented is circular. Lack of an asterisk indicates the molecule is linear.

(3) Junctions between natural boundaries of functional components are indicated by vertical lines along the horizontal lines.

(4) Genes or functional components are indicated.

(5) Distances between genes and restriction sites are not to scale. The charts show the relative positions only unless indicated otherwise.

Most of the recombinant DNA methods employed in practicing the present invention are standard procedures, well known to those skilled in the art, and described in detail, for example, by EP-223452 which is incorporated herein by reference. Enzymes are obtained from commercial sources and are used according to the vendor's recommendations or other variations known to the art. Reagents, buffers, and culture conditions are also known to those in the art. General references containing such standard techniques include the following: R. Wu, ed. (1979) *Methods in Enzymology* Vol. 68; J. H. Miller (1972) *Experiments in Molecular Genetics;* T. Maniatis et al. (1982) *Molecular Cloning: A Laboratory Manual;* and D. M. Glover, ed. (1985) *DNA Cloning* Vol II, all of which are incorporated by reference.

EXAMPLE 1

Isolation of CMV RNAs

Cucumber mosaic virus strain C (CMV-C) was propagated in tobacco plants and RNA was isolated by the method of Lot et al. (Annals of Phytopathology 4:25, 1972).

EXAMPLE 2

Cloning of CMV-C (a) Synthesis of Double-stranded cDNA3

Total CMV-C RNA was polyadenylated in order to provide a site for the annealing of an oligo dT primer. The reaction buffer was as follows: 5 µl, 1M Tris pH 7.9; 1 µl, 1M $MgCl_2$; 2.5 µl, 0.1M $MnCL_2$; 5 µl, 5 µ NaCl; 0.5 µl, 100 nM ATP; 18 µl, 2.8 mg/ml bovine serum albumin. 3.2 µl of this buffer were mixed with 2 µg of CMV-C total RNA. 3.8 µl $H_2O$ and 1 µl of poly-A polymerase were added, and the reaction mixtures were incubated at 37° C. for 10 minutes.

The resulting polyadenylated RNA was used in the cDNA synthesis protocol of Polites and Marotti (Biotechniques 4:514, 1986), except that 0.75 mM KCl was used instead of 50 mM NaCl, and 130 uCi/100 µl $^{32}$P-dCTP was used instead of 10–50 uCi/100 µl.

After ds-cDNA was synthesized, it was purified by G-100 column chromatography, precipitated with ethanol, and suspended in 20 µl of 1X Eco R1 methylase buffer (100 mM NaCl, 100 mM Tris-HCL pH 8.0, 1 mM EDTA, 80 µM S-adenosyl methionine, 100 µg/ml bovine serum albumin). After removal of a 2 µl aliquot for subsequent gel analysis, an additional 1 µl of 32 mM S-adenosyl methione was added to the reaction mixture mix, and 1 µl (20 units) of Eco RI methylase. The reaction was incubated at 37° C. for 30 minutes and stopped by incubation at 70° C. for 10 minutes.

Two µl were removed from the above reaction, and 1 µl (5 units) of *E. coli* DNA polymerase I Klenow fragment was added. The reaction was incubated at 37° C. for 10 minutes, then extracted with phenol/chloroform before precipitating with ethanol. The pellet was washed in 70% ethanol, then in 70% ethanol/0.3M sodium acetate.

The pellet was dried and resuspended in 8 µl 0.5 µg/µl phosphorylated Eco RI linkers (available from Collaborative Research, Inc, 128 Spring Street, Lexington Mass. 02173). One µl 10X ligase buffer (800 mM Tris-HCl pH 8.0, 200 mM $MgCl_2$, 150 mM DTT, 10 mM ATP) and 1 µl of T4 DNA ligase (4 units/µl) were added, and the reaction was incubated overnight at 15° C.

The ligation reaction was then stopped by incubation at 65° C. for 10 minutes. Sixty µl of water, 10 µl of 10X Eco RI salts(900 mM Tris pH 8.0, 100 mM MgCl2, 100 mM NaCl), and 10 µl of EcoRI (10 units/µl) were added, and the reaction was incubated at 37° C. for 1 hr (a 5 µl aliquot was removed at the beginning for subsequent gel analysis). The reaction was stopped by phenol/chloroform and chloroform extraction. A 5 µl aliquot was removed for gel analysis, and half of the remainder was frozen for future use. The other half was purified by G-100 column chromatography. The G-100 fractions containing the cDNA were concentrated by butanol extraction, precipitated with ethanol, and resuspended in 10 µl of $H_2O$. After removing 3 µl for subsequent analysis, 1 µl lambda gt11 arms (available from Stratagene Co., 3770 Tandy St, San Diego, Calif. 92121), 1 µl of 10X ligase buffer, and 1 µl T4 DNA ligase were added, and the reaction was incubated at 15° C. overnight.

The resulting ligated lambda gt11/cDNA molecules were packaged according to the procedure recommended by the manufacturer of the packaging extract (Gigapack plus, also from Stratagene). This yielded recombinant lambda phage, which were plated according to methods known to those skilled in the art.

Lambda clones containing the coat protein gene were identified by hybridization with radioactively labelled single-stranded cDNA from purified RNA 4 of the whiteleaf strain of CMV (obtained from Dr. D. Gonsalves, Cornell University, Geneva, N.Y.). This RNA 4 single-stranded cDNA was synthesized as follows: RNA 4 molecules were polyadenylated as described above for total CMV-C RNA, except that 5.8 µg RNA 4 was used. First strand synthesis was as described by Polites and Marotti (Biotechniques 4:514, 1986) except that non-radioactive dCTP was not included. Instead, 260 uCi/100 µl of radioactive dCTP was used.

The labelled single-stranded cDNA was purified by P6 column chromatography and used to probe replicate filters lifted from the lambda phage plates mentioned above. The single-stranded cDNA hybridized with DNA from several phage clones, indicating that they contained at least a part of the CMV-C coat protein gene. Several of these lambda clones were grown, and DNA from them was isolated according to methods known to those skilled in the art.

EXAMPLE 3

Construction of a pUC19 Clone Containing the CMV-C Coat Protein Gene

Several of the cloned cDNA's mentioned in the above example were transferred to the plasmid vector, pUC19 (available from Bethesda Research, P.O. Box 6009, Gaithersburg, Md. 20877), using standard methods. The cloned fragments in pUC19 were then sequenced by the technique described by Maxam and Gilbert (*Methods in Enzymology* 65:499, 1980). Based on this information, one clone was identified as containing the entire coat protein gene. The sequence of this clone (designated pCMV9.9) is shown in FIG. 1.

EXAMPLE 4

Construction of a Micro T-DNA Plasmid Containing a Plant-expressible CMV-C Coat Protein Gene with the CaMV 35S Polyadenylation Signal In order to attach the CaMV 35S promoter and polyadenylation signal, a fragment extending from the Acc I site (at position 311) to the Eco RI site (at position 1421) was removed from pCMV9.9 and ligated into the multiple cloning site of the vector pDH51 (Pietrzak et al., 1986) (available from Thomas Hohn, Friedrich Miescher Institute, P.O. Box 2543, CH-4002, Basel, Switzerland). This was accomplished by complete Eco RI and partial Acc I digestion of pCMV9.9, creating a blunt-ended molecule out of the appropriate Acc I-Eco RI fragment (using the Klenow fragment of *E. Coli* DNA polymerase I), and ligating it into the Sma I site of pDH51 Chart 1). This clone, designated pDH51/CP19, was sequenced by the Maxam-Gilbert technique to confirm its suitability for expression in plants.

The plant expressible coat protein gene was then moved into a vector suitable for Agrobacterium-mediated gene transfer. An Eco RI-Eco RI fragment was removed from pDH51/CP19 and placed into the Eco RI site of the plasmid, pUC1813 (available from Robert Kay, Dept. of Chemistry, Washington State University, Pullman, Wash.), creating the plasmid pUC1813/CP19. A 1.8 k.b. fragment containing the plant expressible gene was removed by partial Hind III digestion and ligated into the Hind III site of the vector, pGA482 (An et al., 1985) (available from Gynehung An, Institute of Biological Chemistry. Washington State University).

The resulting plasmid was designated pGA482/CP19H (Chart 2). The plant expressible gene for glucuronidase (available from Clontech Laboratories, Inc., 4055 Fabian Way, Palo Alto, Calif.) was then added to pGA482/CP19H by removing a partial Bam HI-Bam HI fragment from a pUC1813 clone containing the gene and inserting it into the Bgl II site of pGA482/CP19. This final construction was designated pGA482/CP19/GUS (Chart 2) and was confirmed by Maxam-Gilbert sequencing.

This plasmid, or its derivatives, can be transferred into Agrobacterium strains A208, C58, LBA4404, C58Z707, A4RS, A4RS(pRi278b) and others. Strains A208, C58, LBA4404, and A4RS are available from ATCC, 12301 Parklawn Drive, Rockville, Md. A4RS(pRi278b) is available from Dr. F. Casse-Delbart, C.N.R.A., Routede Saint Cyr, F78000, Versailles, France. C58Z707 is available from Dr. A. G. Hepburn, University of Illinois, Urbana, Ill.

EXAMPLE 5

Construction of a Micro T-DNA Plasmid Containing a Plant-expressible CMV Coat Protein Gene with the Phaseolin Polyadenylation Signal The 35S polyadenylation signal was replaced by that of phaseolin by removing a Avr II-Xba fragment from pDH51/CP19. This digestion removes a DNA region which includes the 3' terminus of the coat protein clone (however, all of the CMV coat protein coding region remains intact), an artificially introduced stretch of A-residues, and part of the pDH51 polylinker. An Xba I-Xba I fragment from a pUC1813 clone containing the phaseolin polyadenylation signal was used to replace the Avr II-Xba I fragment. This construction was then removed by digestion with Eco-RI, and cloned into the Eco RI site of pUC1813. This pUC1813 clone was then digested with Xba I, and the fragment consisting of the 35S promoter, the coat protein coding region, and the phaseolin polyadenylation signal was ligated into Xba I site of pGA482. The glucuronidase gene was then added as described above to produce the plasmid pGA482/CP19A-/411GUS (Chart 3). The structure of the plasmid was confirmed by Maxam-Gilbert sequencing.

An alternative plasmid (designed to test the effect that the stretch of A-residues have on expression) was constructed by placing the phaseolin polyadenylation signal from pUC1813 (see above) into the Xba I site of pDH51/CP19. A fragment containing the 35S promoter, coat protein coding sequence, and the phaseolin and 35S polyadenylation signals were then removed from pDH51/CP19 by Eco RI digestion, and ligated into pUC1813. A fragment containing the 35S promoter, coat protein coding sequence (including the artificially synthesized stretch of A-residues), and the phaseolin polyadenylation signal was then removed from that plasmid by partial Xba I digestion and ligated to the Xba-I site of pGA482. The glucuronidase gene was subsequently inserted as described above. The resulting plasmid was designated pGA482/CP19/411/GUS (Chart 4), and the structure was confirmed by Maxam-Gilbert sequencing.

These plasmid, or their derivatives, are transferred into Agrobacterium strains A208, C58, LBA4404, C58Z707, A4RS, A4RS(pRi278b) and others which in turn are utilized to insert the CMV-C coat protein genes into plant cells by methods described.

EXAMPLE 6

Transfer of Viral Resistance

The purpose of this example is to generate a construction for the expression of a plant virus coat protein gene which, when expressed in a dicotyledonous plant, results in reduced symptoms or resistance to later infections by that virus (see report by Powell-Abel et al. (1986) *Science* 232:738). Viral coat proteins are isolated from any number of plant virus classes (tobamo, cucumo, poty, tobra, AMV, etc.) and they are expressed constitutively in plants after the attachment of the CaMV 35S promoter. In addition, a plant poly (A) signal is added to the 3' region to ensure proper expression.

A clone containing any specific viral coat protein gene can be obtained for both plant DNA and RNA viruses. Such is the case for cucumber mosaic virus strain C (CMV-C); its RNA genome was copied into double-stranded cDNA and the coat protein gene was isolated and characterized as follows. A poly(A) region was added to the 3' end of CMV-C total RNA, using *E. coli* polyadenylase. This poly (A) region was used to anneal an aligo dT primer which was used to prime the synthesis of single-stranded (SS) cDNA using reverse transcriptase and appropriate buffer of CMV-C SS-cDNA, double-stranded cDNA was synthesized by adding RNase H to remove the RNA from the duplex and the second strand was made by adding *E. coli* DNP polymerase I (Klenow fragment) and the appropriate buffer. After synthesis of CMV-C ds-DNA, it was *E. coli* methylated using Eco RI methylase and Eco methylent buffer, thus protecting all internal Eco RI sites in the CMV-C ds-cDNA molecules. After Eco R7 methylation the CMV-C ds-cDNA molecules were treated again with *E. coli* polymorase I (Klenow fragment) to ensure that all ends (5' and 3') were flush, then these molecules were ligated to Eco RI linkers using T4-Ligase. After ligation the CMV-C ds-cDNA molecules were separated from contaminating linker by size fractionation on a G50 column (1 cm×30 cm). The fraction containing the majority of the CMV-C ds-cDNA molecules was EtOH precipitated, followed by resuspension in 10 μg of H20. About 100 μg of these Eco RI linked CMV-C ds-cDN molecules were removed and mixed with 1 μg of λ gT11 arms (commercially available) and ligated together using T4 ligase. The recombinant gT 11-CMV-C were plated using *E. coli* Dp50supF as host and these plates ($10^{-4}$ clones) were screened for clones containing CMV-C coat protein gene coding region using 32p-labeled CMV-whiteleaf SS-cDNA as probe. From this screening, a clone, λ gT11-CMV9.9 was isolated. It contained an EcoRI insert of 1400 base pair, enough to encode the complete CMV coat protein. This CMV coat protein gene can be expressed in plant tissues once a plant-functional promoter and poly (A) signal are attached to its 5' and 3' regions, respectively. The scheme to accomplish this is shown in Chart 5.

Attachment of the constitutive cauliflower mosaic virus (CaMV) 35S promoter was done by first doing a partial AccI and Complete EcoRI digests of clone pCMV9.9 which was obtained by cloning the Eco RI insert from Lambda gT11-CMV9.9 into Eco RI cut pUC 19(commercially available). The 1100 bp CMV-C coat protein gene fragment was removed, both ends were blunted, and this fragment was cloned into the Sma I site of pDH51 [(Pietrzak et al. (1986). *Nuc. Acids Res.* 14:5857) which is available from T. Hohn, Friedrick Mieschen Institut, Basel, Switzerland] to obtain clone pDH51/cP19. This positioned the CMV-C coat protein gene downstream of the CaMV 35S promoter and upstream from the CaMV poly (A) signal sequence. To ensure a high level of expression other poly (A) signal sequences (which may function better than the CaMV 35S poly (A) signal) can be attached, such as the poly (A) signal from the seed storage protein gene phaseolin (Slightom et al. (1983) *Proc. Natl. Acad. Sci.* 80:1897). To facilitate engineering, this plant expressible CMV-C coat protein gene was removed from clone pDH51/CP19 by an Eco RI digest and the 1800 bp fragment was cloned into pUC1813 (which contains more restriction enzyme sites and is available from Dr. R. Kay, Washington State University, Pullman, Wash.). The resulting clone, pUC1813/CP19, was then partially digested with HindIII and the 1800 bp fragment was cloned into the binary vector pGA482 to obtain the new clone, pGA482/CP19H (see Chart 5). This binary plasmid, or its derivatives, can be transferred into Agrobacterium strains: A208, C58, LBA4404, C58Z707, A4RS, A4RS(pRiB28b) and others. Using the transformation method of this invention, this plant expressible CMV-C coat protein gene (or any other plant virus coat protein gene) can be transferred into a dicotyledonous plant species such as, cucumber, squash, melon, zucchini, pepper, etc. The development of these new cultivars are useful because of their resistance to infections by specific virus or viruses (if more than one virus coat protein gene construction is transferred to a single plant).

Chart 1 pCMV9.9 — coat protein gene — A residues

↓ pDH51/CP19 — CaMV 35S promoter — coat protein gene — A residues — CaMV 35S poly-A signal Chart 2

Construction of pGA482/CP19H/GUS pDH51/CP19 — CaMV 35S promoter — coat protein gene — A residues — CaMV 35S poly-A signal

↓ pGA482/CP19H — BR — NOS-NPTII — CaMV 35S promoter — coat protein gene — A residues — CaMV 35S poly-A signal — BL

↓ pGA482/CP19H/GUS — BR — NOS-NPTII — coat protein gene — A residues — gus gene — CaMV 35S poly-A signal — BL Chart 3
Construction of pGA482/CP19A-/411/GUS
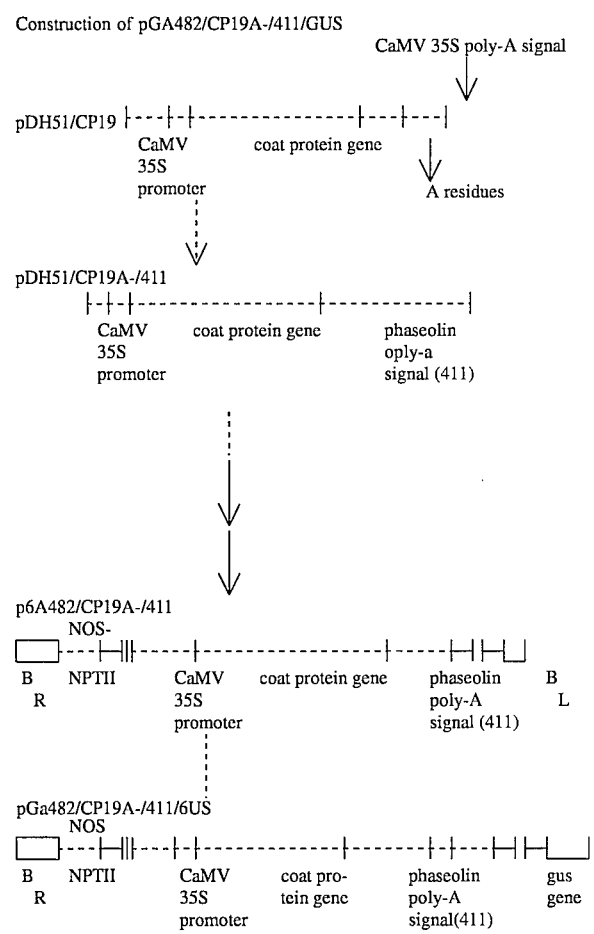
Chart 4
Construction of pGA482/CP19/411/GUS
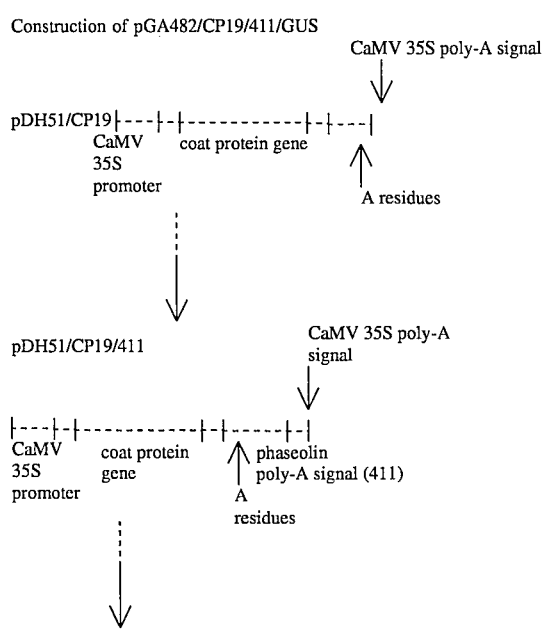
-continued
Chart 4
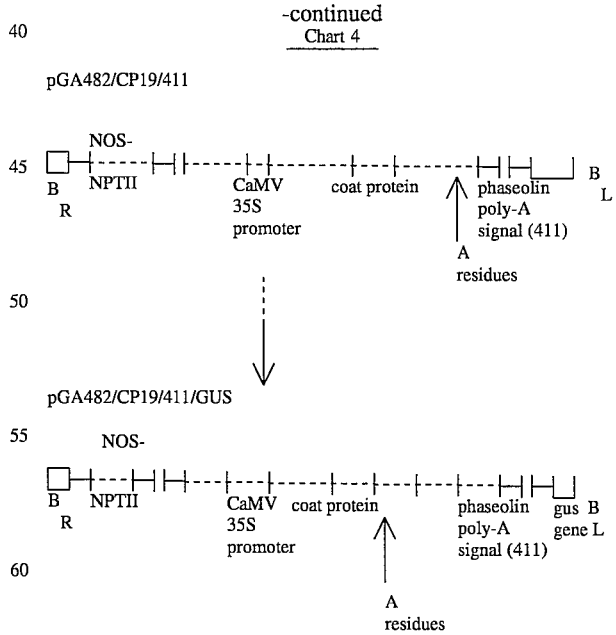

Chart 5
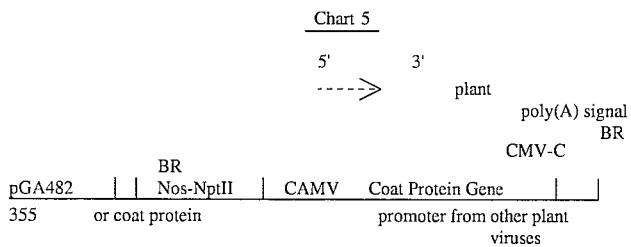
We claim:
1. A DNA comprising the sequence shown in FIG. 1, said sequence encoding the coat protein from the C strain of cucumber mosaic virus.

2. A plant transformation vector comprising the DNA according to claim 1, a CaMV 35S promoter of cauliflower mosaic virus and the polyadenylation signal of either the cauliflower mosaic 35S gene or phaseolin seed storage gene and in which the promoter, the DNA and polyadenylation signal are operably joined in a 5' to 3' direction.

3. A bacterial cell containing the plant transformation vector of claim 2.

4. A transformed plant cell containing the plant transformation vector of claim 2.

5. A plant selected from the families cucurbitaceae or solanaceae comprising transformed cells of claim 4.

6. A cucurbitaceae plant according to claim 5.

7. A solanaceae plant according to claim 5.

* * * * *